(12) United States Patent
Ishikawa et al.

(10) Patent No.: US 11,317,809 B2
(45) Date of Patent: May 3, 2022

(54) IMAGING APPARATUS

(71) Applicant: SHIMADZU CORPORATION, Kyoto (JP)

(72) Inventors: Akihiro Ishikawa, Kyoto (JP); Kazushige Tachibana, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 1159 days.

(21) Appl. No.: 15/689,641

(22) Filed: Aug. 29, 2017

(65) Prior Publication Data
US 2019/0059735 A1 Feb. 28, 2019

(51) Int. Cl.
*A61B 5/00* (2006.01)
*G01N 21/64* (2006.01)
*A61B 90/50* (2016.01)
*A61B 5/02* (2006.01)

(52) U.S. Cl.
CPC ............ *A61B 5/0071* (2013.01); *A61B 90/50* (2016.02); *G01N 21/6456* (2013.01); *A61B 5/02007* (2013.01); *A61B 5/4244* (2013.01); *A61B 5/445* (2013.01); *A61B 2560/0437* (2013.01); *G01N 2021/6439* (2013.01)

(58) Field of Classification Search
None
See application file for complete search history.

(56) References Cited

U.S. PATENT DOCUMENTS

| | | | | |
|---|---|---|---|---|
| 9,101,319 B2* | 8/2015 | Kojima | ............... | A61B 6/547 |
| 9,414,795 B2* | 8/2016 | Nakata | ............... | A61B 6/4411 |
| 2013/0039473 A1* | 2/2013 | Kojima | ............... | A61B 6/547 |
| | | | | 378/91 |
| 2015/0018622 A1* | 1/2015 | Tesar | ............... | A61B 90/20 |
| | | | | 600/202 |
| 2015/0069256 A1* | 3/2015 | Nakata | ............... | A61B 6/4411 |
| | | | | 250/393 |

(Continued)

FOREIGN PATENT DOCUMENTS

| | | |
|---|---|---|
| JP | 2000-296101 | 10/2000 |
| JP | 2011-249267 | 8/2011 |
| JP | 2012170641 A | 9/2012 |

(Continued)

OTHER PUBLICATIONS

JP 2015-089962, Notification of Reasons for Refusal, dated Jul. 11, 2019, 3 pages—English, 3 pages—Japanese.

(Continued)

*Primary Examiner* — Luther Behringer
(74) *Attorney, Agent, or Firm* — Andrew F. Young, Esq.; Nolte Lackenbach Siegel

(57) ABSTRACT

An imaging apparatus that is easily moved between locations protects an imaging element in motion and provides a first arm member and a proximate movable second arm member. A lighting-imaging element is movably positionable proximate an arm mechanism and also proximate a rear-side location of a wheeled platform relative to a traveling direction thereby preventing damage. The first and second arm are relatively surrounded with a sub-arm and lighting-imaging element, thereby preventing further unintended movement. Accordingly, an elongating (separation) of the first and second arm members are prevented.

4 Claims, 4 Drawing Sheets

(56) References Cited

U.S. PATENT DOCUMENTS

2015/0327765 A1\* 11/2015 Crane ................ H04N 5/23296
                                                              348/77

FOREIGN PATENT DOCUMENTS

| JP | 2015-507493 | 3/2015 |
| WO | WO 2009/139466 | 9/2011 |
| WO | WO 2013/096850 | 6/2013 |

OTHER PUBLICATIONS

JP 2018-175793, Notice of Reasons for Refusal, dated Aug. 24, 2020, 4 pages—Japanese, 4 pages—English.
JP 2015-089962, Notification of Reasons for Refusal, dated Mar. 26, 2018, 3 pages—English.

\* cited by examiner

IMAGING APPARATUS

CROSS REFERENCE TO RELATED APPLICATIONS

This application relates to, but does not claim priority from, JP 2015-089962 filed Apr. 27, 2015, the entire contents of which are incorporated herein fully by reference.

FIGURE SELECTED FOR PUBLICATION

FIG. 2

BACKGROUND OF THE INVENTION

Field of the Invention

The present invention relates to an imaging apparatus that irradiates excitation light to a fluorescent dye (fluorophore) injected into a subject and images fluorescence emitted from the fluorophore therein.

Description of the Related Art

A method called near-infrared fluorescence (NIF) imaging is applied in a surgery. According to the near-infrared fluorescence imaging, indocyanine green (ICG) as the fluorophore is injected into an affected area. And when a near-infrared light as an excitation light having wavelength approximately 810 nm (nanometers) is irradiated as an excitation light to indocyanine green, indocyanine green emits fluorescence in the near-infrared region in which the peak of the wavelength is approximately 845 nm. Such fluorescence is imaged by an image pickup element capable of detecting the near-infrared light, and then the image thereof is displayed on a display such as a liquid crystal display panel and so forth. According to such near-infrared fluorescence imaging, blood vessels and lymphatic vessels and so forth, which are approximately 20 mm (millimeters) below the body surface, can be observed.

Such near-infrared fluorescence imaging is applied to a tumor surgery and so forth. For example, when the surgical operation for breast cancer is performed relative to breast surgery, the location of the sentinel lymph node must be identified.

The sentinel lymph node is the first lymph node to which a cancer cell reaches ire the lymphatic circulation (lymph flow). When no cancer cell is found in the sentinel lymph node, it can be decided that no metastasis of breast cancer to axillary lymph nodes takes place, so that an axillary lymph nodes dissection can be skipped. Therefore, identification of the location of such sentinel lymph node by using the near-infrared fluorescence imaging is quite effective.

In addition, it is noticeable mainly in the cerebral surgery field that a method using fluorescently-labeled tumor, in which a specific fluorescence dye (fluorophore) is applied, has been applied to a surgical navigation. 5-ALA (5-Aminolevulinic Acid) is used for such fluorescence dye. When 5-Aminolevulinic Acid (5-ALA) is applied, the 5-ALA administered inside the patient's body changes to protoporphyrin (IX/PpbIX), which is a fluorescent substance. Such PpbIX is cumulated specifically and inherently in a tumor. In addition, when visible light having approximately 410 nm wavelength is irradiated to the PpIX, which is a metabolite of 5-ALA, red light having approximately 630 nm wavelength is emitted from the PpIX as fluorescence. Accordingly, if the fluorescence from PpIX is measured (observed), cancer metastasis can be likely confirmed.

Patent Document 1 discloses a data collection method for collecting the data of the area undetectable in the affected cancer area distribution image as the sub-affected cancer area data despite detectable in the strength-distribution image using the near-infrared fluorescence by comparing the near-infrared fluorescence strength-distribution image obtained by irradiating the excitation light for indocyanine green to the body's target organ in which indocyanine green is injected, and the cancer affected area distribution image obtained by applying an X-ray, a nuclear magnetic resonance or an ultrasound wave relative to the target organ before injecting indocyanine green.

RELATED PRIOR ART DOCUMENTS

Patent Document

PATENT DOCUMENT 1: PCT International Publication No. WO2009/139466

ASPECTS AND SUMMARY OF THE INVENTION

In one aspect of the present invention, there is provided an imaging apparatus that is easily moved and capable of imaging at an arbitrary location and of which imaging element is protected from collision with the wall and so forth is provided. As will be discussed in more detail below, a first arm member and a second arm member relative to the arm mechanism are in the waiting position in which the first arm member and the second arm member are nearby each other, and in addition, a lighting-imaging element relative to the arm mechanism is in-place in the rear-side location of the wheeled platform in the traveling direction thereof. Consequently, the lighting-imaging element relative to the arm mechanism is in-place in the rear-side location of a wheeled platform in the traveling direction thereof, so that a collision of the imaging element with the wall and so forth can be prevented despite moving of the apparatus. In addition, the first arm member and the second arm member relative to the arm mechanism are surrounded with a sub-arm 41 and a lighting-imaging element. Accordingly, when moving the apparatus, it is feasible to prevent the undesirable elongation (separation) of the first arm member and the second arm member.

Objects to be Solved

It is preferable that the imaging apparatus per se is movable to widely utilize such imaging apparatus that images the fluorescence from such fluorescence dye. Accordingly, a movable wheeled platform having wheels as the imaging apparatus is considered and adopted. In addition, relative to such imaging apparatus that images florescence from the fluorescence dye, an assistant may hold the imaging element to image the fluorescence by hand, but it is preferable that the imaging apparatus comprises an arm mechanism capable of securing the imaging element at the predetermined location. Therefore, it is an option that such imaging apparatus has a wheeled platform having wheels and wherein the imaging element is connected to the wheeled platform with the arm mechanism. Further, the arm mechanism is preferably foldable for saving the installation space and so forth.

On the other hand, when such constitution is adopted and the imaging apparatus having the wheeled platform structure is moved to the imaging location to image a subject, it is preferable that the imaging element is installed in the front side of the wheeled platform relative to the traveling, direction thereof. Therefore, the imaging element is projected in the front side of the wheeled platform relative to the traveling direction thereof from the upper side of the wheeled platform. When the imaging apparatus having such featured structure is adopted and such imaging apparatus moves, the projected imaging element may be an obstacle likely resulting in causing collision with a wall and so forth.

The purpose of the present invention is to resolve above such problem and to provide an imaging apparatus that facilitates to move and images at an arbitrary location and additionally, collision of the imaging element with the wall and so forth can be prevented despite moving of the imaging apparatus.

Means for Solving the Problem

According to the invention an imaging apparatus that irradiates excitation light to the fluorescent dye (fluorophore) injected into the body of a subject and images fluorescence emitted from the fluorophore therein comprises a movable wheeled platform having wheels, a first arm members swingable (capable of being oscillated) relative to the wheeled platform, and a second arm members that is connected to the tip of the first arm member is swingable relative to the first arm member; and further comprises an arm mechanism that allows the first arm member and the second arm member to take an imaging position (posture) having a predetermined open angle from the center of the connection element of the first arm member and the second arm member, an arm member that allows the first arm member and the second arm member to take a waiting position (posture) in which the first arm member and the second arm member are nearby each other; an imaging element that images the fluorescence; and a sub arm, which is installed revolvably to the tip of the second arm member in the arm mechanism under a state in which the imaging element is being supported, that moves the imaging element between the front-side location of the wheeled platform in the traveling direction thereof relative to the arm mechanism and the rear-side location of the wheeled platform in the traveling direction thereof relative to the arm mechanism.

According to another aspect of the present invention, there is provided an imaging apparatus, wherein when the arm mechanism is the waiting position, the first arm member and the second arm member are surrounded with the sub-arm and the imaging element by that the sub-arm shifts the imaging element to the rear-side location of the wheeled platform in the traveling direction thereof relative to the arm mechanism.

Effect of the Invention

According to the invention of the claim 1, the movement is facilitated by the effect of the wheeled platform having wheels, so that it is feasible that an imaging is performed at an arbitrary location. At this time, the imaging element moves from the front-side location to the rear-side location in the traveling direction of the wheeled platform, so that a collision of the imaging element with the wall and so forth can be prevented despite moving the imaging apparatus.

According to the invention of the claim 2, when the arm mechanism is in the waiting position, the sub-arm moves to surround the first arm member and the second arm member with the sub-arm and the imaging element, so that it is feasible that elongation (separation) of the first arm member and the second arm member is prevented and the safety and security of the apparatus are improved.

It will be further understood that as noted herein, the movements of revolvability and hinged connections allow the first arm and second arm to have multiple degrees of freedom relative to the wheeled cart, the sub-arm as well. As a result, at least three degrees of movement for the dynamic system exist that enable operation.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
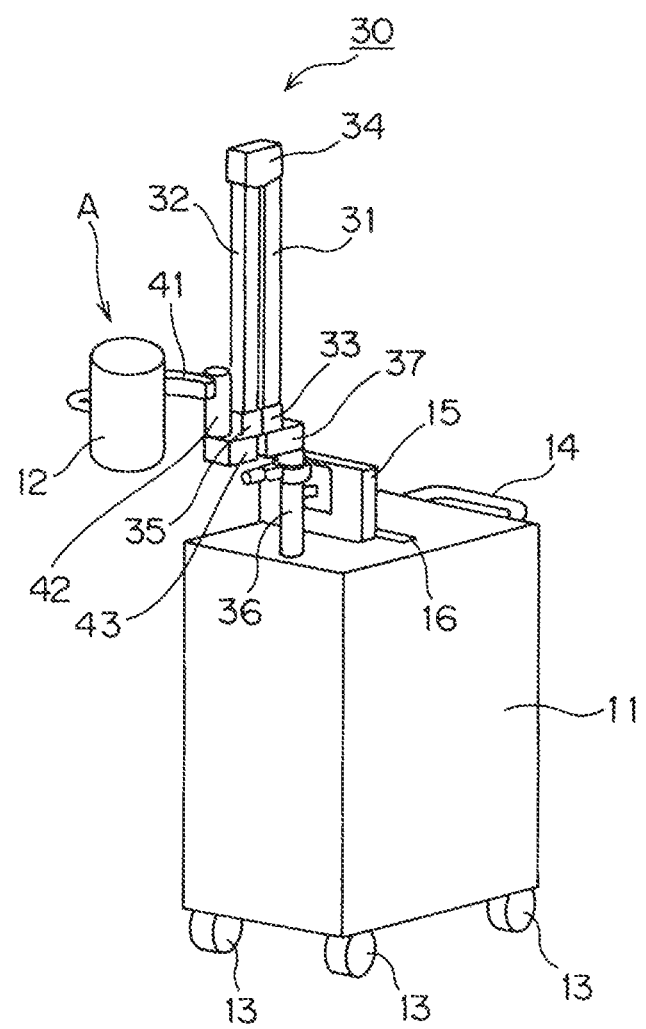
FIG. 1 is a schematic perspective view of an imaging apparatus according to the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

If used herein, a "computer-based system" comprises an input device for receiving data in any form, an output device for outputting data in any tangible form (e.g. printing, transmitting, relaying, calculating, or displaying on a computer screen), a memory for storing data as well as computer code, and a microprocessor for executing computer code wherein said computer code resident in said permanent memory will physically cause said microprocessor to read-in data via said input device, process said data within said microprocessor and output said processed data via said output device.

It will be further understood by those of skill in the art that the apparatus and devices and the elements herein, without limitation, and including the sub components sue as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the movement, guidance, control and operational systems and devices and subcomponents noted herein and structures that accomplish the functions without restrictive language or label requirements since those of skill in the art are well versed in related, diagnostic devices, computer and operational controls and technologies of radiographic devices and all their sub components, including various circuits and combinations of circuits without departing from the scope and spirit of the present invention.

Figure 2:
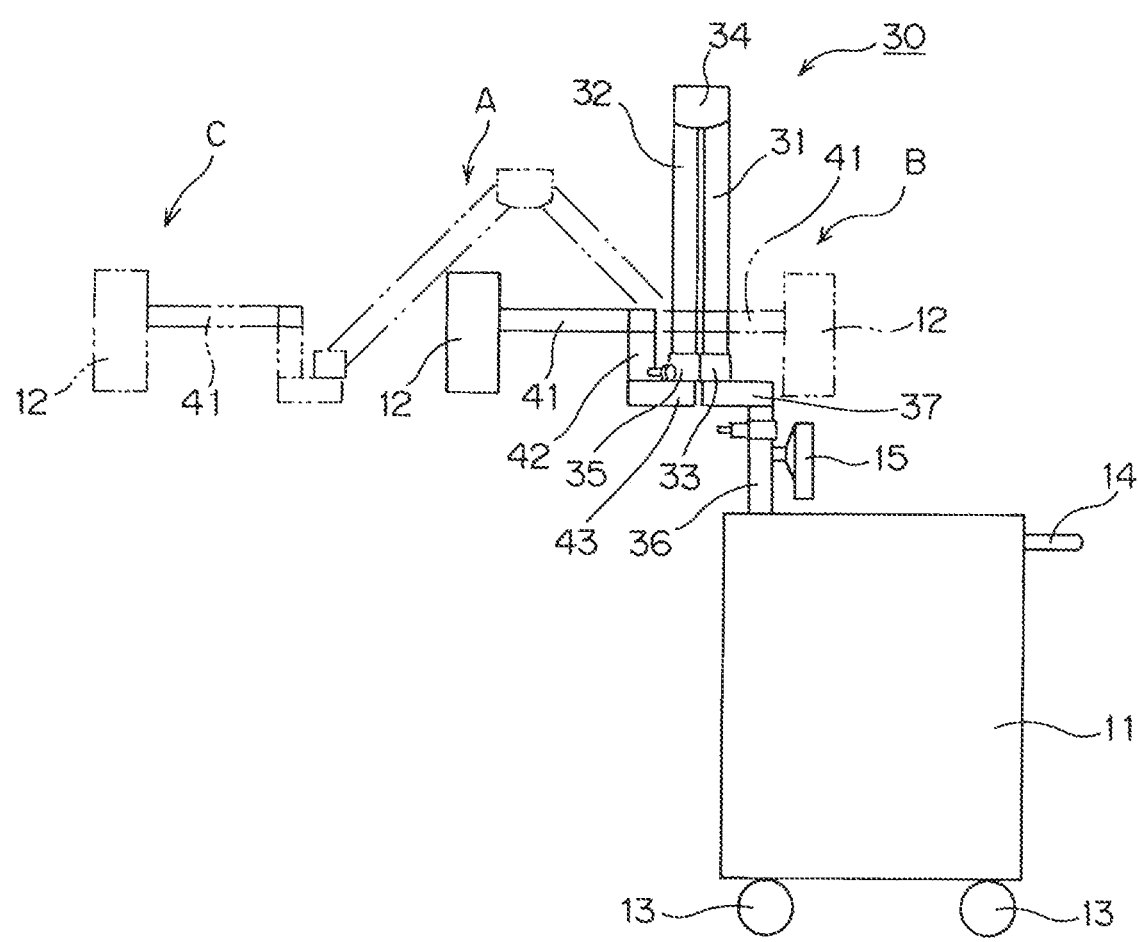
FIG. 2 is a schematic side view of the imaging apparatus according to the present invention.
Figure 3:
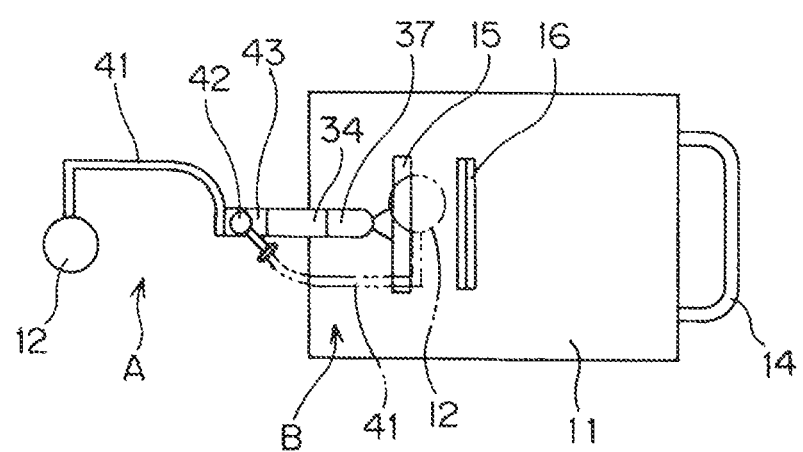
FIG. 3 is a schematic plan view of the imaging apparatus according to the present invention.

The inventor sets forth Embodiments of the present invention based on the following FIGS. FIG. 1 is the schematic perspective view of the imaging apparatus according to the present invention. FIG. 2 is the schematic side view of the imaging apparatus according to the present invention. FIG. 3 is the schematic plan view of the imaging apparatus according to the present invention.

The imaging apparatus according to the present invention that irradiates the excitation light to the fluorescence dye (fluorophore) injected into the body and images the fluorescence emitted from the fluorophore comprises a wheeled platform 11 having four wheels 13, an arm mechanism 30 installed on the upper-side of wheeled platform 11 and nearby the front (left direction in FIG. 2, FIG. 3) of the wheeled platform 11 in the traveling, direction thereof, a lighting-imaging element 12 installed to the arm mechanism 30 via the sub-arm 41, and a monitor 15. A handle 14, which is used when the wheeled platform is moved, is installed to the rear of the wheeled platform in the traveling direction thereof. In addition, a concave portion 16 on the upper-side of the wheeled platform 11 is formed to mount a remote controller to operate remotely the imaging apparatus.

The arm mechanism 30 set forth above is installed to the front-side of the wheeled platform 11 in the traveling direction thereof. Such arm mechanism 30 comprises the first arm member 31 connected to the support element 37 installed on the support pole 36, which is installed and standing in the front-side of the wheeled platform 11 in the traveling direction thereof, with a hinge 33. The first arm member 31 is swingable relative to the wheeled platform 11 via the support pole 36 and the support element 37 due to the action of the hinge 33. In addition, the monitor 15 set forth above is attached to the support pole 36.

The second arm member 32 is connected to the upper end of the first arm member 31 with a hinge 34. The second arm member 32 is swingable relative to the first arm member 31 due to the action of the hinge 34. Accordingly, referring to FIG. 2, as indicated by the virtual line (chain double-dashed line) having the reference sign C, the imaging position in which the first arm member 31 and the second arm member 32 open at the predetermined angle relative to the hinge 34, which is the connection element of the first arm member 31 and the second arm member 32, as the center, and the waiting position, indicated by the solid line in FIG. 1-FIG. 3 having the reference sign A, in which the first arm member 31 and the second arm member 32 are nearby each other, can be provided.

The support element 43 is connected to the bottom end of the second arm member 32 with a hinge 35. The support element 43 is swingable relative to the second arm member 32 due to the action of the hinge 35. The support element 43 supports the revolving axis 42. Then, the sub-arm 41 supporting the lighting-imaging element 12 revolves around the revolving axis 42 as the center, which is installed to the tip of the second arm member 32. Therefore, the lighting-imaging element 12 shifts along with revolving of the sub-arm 41 between the front-side location of the wheeled platform 11 in the traveling direction thereof relative to the arm mechanism 30, as indicated by the solid line with the reference sign A in FIG. 1-FIG. 3 or the virtual line (chain double-dashed line) in FIG. 2 with the reference sign C, and the rear-side location of the wheeled platform 11 in the traveling direction thereof relative to the arm mechanism 30, as indicated by the virtual line (chain double-dashed line) with the reference sign B in FIG. 2 and FIG. 3.

The first arm member 31 and the second arm member 32 relative to the arm mechanism 30 are surrounded with the sub-arm 41 and the lighting-imaging element 12 at the waiting position; at which the first arm member 31 and the second arm member 32 are nearby each other as indicated by the solid line with the reference sign A in FIG. 1-FIG. 3, and in addition, in the state, in which the lighting-imaging element 12 is in-place in the rear-side of the wheeled platform 11 in the traveling direction thereof relative to the arm mechanism 30 as indicated by the virtual line with the reference sign B in FIG. 2 and FIG. 3

Figure 4:
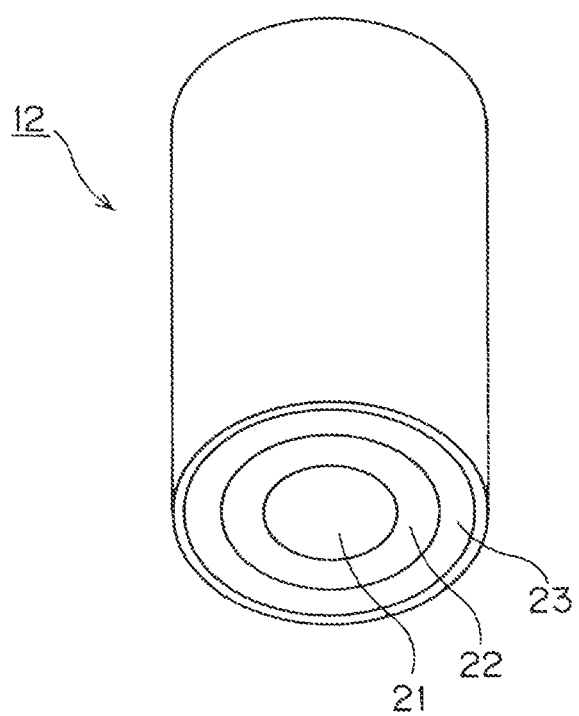
FIG. 4 is a schematic view of the lighting-imaging element 12.

FIG. 4 is the schematic view of the lighting-imaging element 12.

The lighting-imaging element 12 further comprises an imaging element 21 having a plurality of image pickup devices capable of imaging visible light and near-infrared light, a first light source 22 installed in the circumference of the imaging element 21 and a second light source 23 installed in the circumference of the first light source 22. The first light source 22 irradiates near-infrared light having the wavelength 810 nm, which is an excitation light to excite indocyanine green as a fluorescence dye. The indocyanine green, to which the near-infrared light having the wavelength 810 nm is irradiated, emits a near-infrared light as fluorescence having a peak wavelength approximately 845 nm. In addition, the second light source 23 irradiates white light (visible light).

Further, according to the aspect of the present Embodiment, the lighting-imaging element 12 having unified the first light source 22 and the second light source 23 and the imaging element 21 is used, but the first light source 22 and the second light source 23 and the imaging element 21 can be independently arranged and installed.

When the surgical, operation is performed using the imaging apparatus having such structure set forth above, the operator operates the handle 14 to move the wheeled platform 11 and move the imaging apparatus to the location at which the surgery is performed.

At this time, the first arm member 31 and the second arm member 32 relative to the arm mechanism 30 are nearby each other as indicated by the solid line with the reference sign A in FIG. 1-FIG. 3 are in the waiting position and in addition, the lighting-imaging element 12 is in-place in the rear-side of the wheeled platform 11 in the traveling direction thereof relative to the arm mechanism 30 as indicated by the virtual line with the reference sign B in FIG. 2 and FIG. 3.

Consequently, the lighting-imaging element 12 relative to the arm mechanism 30 is in-place in the rear-side location of the wheeled platform 11 in the traveling direction thereof, so that a collision of the imaging element 12 with the wall and so forth can be prevented despite moving of the apparatus. In addition, under such condition, the first arm member 31 and the second arm member 32 relative to the arm mechanism 30 are surrounded with the sub-arm 41 and the lighting-imaging element 12. Accordingly, when moving the apparatus, it is feasible that the elongation (separation) of the first arm member 31 and the second arm member 32 is prevented.

Next, the sub-arm 41 revolves around the revolving axis 42 as the center thereof so that the lighting-imaging element 12 relative to the arm mechanism 30 can be in-place is in the front-side of the wheeled platform 11 in the traveling direction thereof as indicated by the solid line with the reference sign A in FIG. 1-FIG. 3. Then, as indicated by the virtual line with the reference sign C it FIG. 2, the first arm member 31 and the second arm member 32 shifts the lighting-imaging element 12 to the location facing to the subject in the imaging position in which the first arm member 31 and the second arm member 32 open by the predetermined angle.

Subsequently, once the setting of the imaging apparatus is completed, indocyanine is injected to the subject with an injection needle. Then after, the near-infrared light as the excitation light is irradiated from the first light source 22 toward the affected area of the subject. Therefore, indocyanine green injected inside body of the subject emits the fluorescence in the near-infrared area of which the peak of the wavelength is at approximately 845 nm. Under such condition, the imaging element 21 of the lighting-imaging element 12 images the proximity of the affected area of the subject.

A fluorescent image taken by the imaging element 21 is displayed on the monitor 15. In addition, such fluorescent image is displayed on the large display installed separately from the imaging apparatus. At this time, the visible image of the subject taken using the imaging element 21 can be displayed on the monitor 15 together with the fluorescent image or after synthesized with the fluorescent image.

When the use of the imaging apparatus is over, the first arm member 31 and the second arm member 32 relative to the arm mechanism 30 returns to the waiting position, in which the first arm member 31 and the second arm member 32 are nearby each other as indicated by the solid line with the reference sign A in FIG. 1-FIG. 3, and in addition, the lighting-imaging element 12 is in-place in the rear-side of the wheeled platform 11 in the traveling direction thereof relative to the arm mechanism 30 as indicated by the virtual line with the reference sign B in FIG. 2 and FIG. 3. Then, the operator operates the handle 14 to move the imaging apparatus to the necessary location.

In addition, according to the Embodiment set forth above, indocyanine is applied to the fluorescence dye, but other fluorescence dye such as 5-ALA set forth above can be applied.

REFERENCE OF SIGNS

11 Wheeled platform
12 Lighting-imaging element
13 Wheel
14 Handle
15 Monitor
21 Imaging element
22 First light source
23 Second light source
30 Arm mechanism
31 First arm member
32 Second arm member
33 Hinge element
34 Hinge element
35 Hinge element
36 Supporting post
41 Sub-arm
42 Revolving axis Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An imaging apparatus, configured to irradiate a fluorescent dye injected into a body of a subject with an excitation light and configured to image a fluorescence emitted from said fluorescent dye during a use, comprising:
   a movable wheeled platform having wheels;
   a first arm member pivotably and extendably swingable relative to said wheeled platform;
   a second arm member provided proximate to a tip end of said first arm member, pivotably and extendably swingable relative to said first arm member, the first arm member defining a first lengthwise axis the second arm member defining a second lengthwise axis;
   a connection element provided between said first arm member and said second arm member, the connection element being configured to transition said first arm member and said second arm member among a plurality of positions, the plurality of positions including an imaging position and a waiting position, the imaging position having a predetermined relative open angle from a center of the connection element;
   an imaging element configured to image the fluorescence;
   a sub-arm, supporting said imaging element, revolvably installed on a tip end of said second arm member; and
   a revolving axis, extending in a vertical direction, provided between the second arm member and the sub-arm;
   wherein said sub-arm has a first position in which said sub-arm curves around a rear-side location of said movable wheeled platform in a traveling direction of the movable wheeled platform when in the waiting position, thereby inhibits the first arm and the second arm from transitioning to the imaging position and said sub-arm is revolvable relative to the revolving axis to a second position in which said sub-arm is disposed at a front-side location of said movable wheeled platform in the traveling direction to permit the first arm and the second arm to transition to the imaging position.

2. The imaging apparatus, according to claim 1, wherein: the connection element is configured to facilitate transitioning of the first arm member and the second arm member between and including:
   (a) the waiting position in which said first lengthwise axis of said first arm member and said second lengthwise axis of said second arm member are parallel to one another; and
   (b) the imaging position.

3. The imaging apparatus, according to claim 2, wherein: the connection element restricts the predetermined relative open angle of the imaging position to no more than 180 degrees.

4. The imaging apparatus, according to claim 1, further comprising:
   a concave portion formed in an upper-side portion of the movable wheeled platform; and
   a remote controller mountable within the concave portion, the remote controller configured to remotely operate the imaging element.

\* \* \* \* \*